US008728799B2

(12) United States Patent
Schmitt

(10) Patent No.: US 8,728,799 B2
(45) Date of Patent: May 20, 2014

(54) APPARATUS AND METHOD FOR ISOLATING HISTOLOGICAL SECTIONS PRODUCED WITH A MICROTOME

(75) Inventor: Christoph Schmitt, Schriesheim (DE)

(73) Assignee: Leica Biosystems Nussloch GmbH, Nussloch (DE)

( * ) Notice: Subject to any disclaimer, the term of this patent is extended or adjusted under 35 U.S.C. 154(b) by 1175 days.

(21) Appl. No.: 12/349,321

(22) Filed: Jan. 6, 2009

(65) Prior Publication Data

US 2009/0181457 A1  Jul. 16, 2009

(30) Foreign Application Priority Data

Jan. 10, 2008  (DE) .......................... 10 2008 000 035

(51) Int. Cl.
   *G01N 1/30*   (2006.01)
   *G01N 33/48*  (2006.01)
   *C12M 1/00*   (2006.01)
   *B26D 7/06*   (2006.01)
   *G01N 1/06*   (2006.01)

(52) U.S. Cl.
   CPC ............... *G01N 1/06* (2013.01); *Y10S 83/9155* (2013.01)
   USPC ....... 435/283.1; 435/40.52; 83/100; 83/915.5

(58) Field of Classification Search
   CPC ............ G01N 1/06; G01N 1/36; G01N 1/42; G01N 2001/065; G01N 35/0009; G01N 35/04; A61L 2/24; B01L 7/50
   USPC .................... 435/40.52, 283.1; 83/100, 915.5
   See application file for complete search history.

(56) References Cited

U.S. PATENT DOCUMENTS

| 3,191,476 | A  |   | 6/1965 | McCormick |
|-----------|----|---|--------|-----------|
| 5,255,585 | A  |   | 10/1993 | Gordon   |
| 5,740,708 | A  |   | 4/1998 | Tabone    |
| 5,746,855 | A  |   | 5/1998 | Bolles    |
| 8,025,842 | B2 | * | 9/2011 | Nakajima et al. ............... 422/65 |

FOREIGN PATENT DOCUMENTS

| DE | 1 748 387 | 7/1957 |
|----|-----------|--------|
| DE | 20 28 898 | 12/1971 |
| DE | 25 06 255 | 9/1976 |
| DE | 694 02 197 | 9/1997 |

(Continued)

OTHER PUBLICATIONS

Search Report from corresponding GB application 0820459.6 dated Feb. 26, 2009 issued by the Great Britain Patent and Trademark Office.

(Continued)

*Primary Examiner* — Narayan Bhat
(74) *Attorney, Agent, or Firm* — Schlee IP International, P.C.; Alexander R. Schlee

(57) ABSTRACT

An apparatus and a method for isolating histological sections produced with a microtome and a microtome are suggested. A previously and currently produced histological section are connected to form a section strip. In order to simplify isolating the previously and currently produced histological sections from each other a nozzle device is provided by means of which the histological sections when positioned on a blade holder are subjected to an air stream of adjusted direction and intensity so that the previously produced histological section of the section strip is separated from the currently produced histological section that is positioned on the blade holder and is removed from the blade holder.

17 Claims, 5 Drawing Sheets

(56) References Cited

FOREIGN PATENT DOCUMENTS

| | | |
|---|---|---|
| DE | 198 03 996 | 9/1998 |
| DE | 69229133 | 1/2000 |
| DE | 102 42 275 | 4/2004 |
| DE | 103 52 578 | 3/2005 |
| DE | 102008000035 | 7/2009 |
| EP | 0 725 712 | 8/1996 |
| EP | 0725712 | 8/1996 |
| EP | 1 094 310 | 4/2001 |
| GB | 1 335 431 | 10/1973 |
| JP | 09101242 | 4/1997 |
| JP | 2002031586 | 1/2002 |
| JP | 2006052963 | 2/2006 |
| JP | 2006220559 | 8/2006 |
| WO | 93/05936 | 4/1993 |
| WO | 94/28390 | 12/1994 |

OTHER PUBLICATIONS

Related non-published U.S. Appl. No. 12/349,411, filed Jan. 6, 2009 and assigned to Leica Biosystems Nussloch GmbH.

Related non-published U.S. Appl. No. 12/341,710, filed Dec. 22, 2008 and assigned to Leica Biosystems Nussloch GmbH.

\* cited by examiner

APPARATUS AND METHOD FOR ISOLATING HISTOLOGICAL SECTIONS PRODUCED WITH A MICROTOME

CROSS-REFERENCE TO RELATED APPLICATION

This application claims the priority of the German patent application DE 102008000035.3 having a filing date of Jan. 10, 2008.

BACKGROUND OF THE INVENTION

The present invention relates to an apparatus for isolating histological sections produced with a microtome. The histological sections are producible in such a way that a histological section that is produced, and is then as a rule positioned on the blade holder, is connected to a previously produced histological section to form a section strip. The present invention further relates to a microtome and to a method for isolated histological sections.

Microtomes have been known for a long time in the existing art. With them, thin histological sections are produced from tissue samples embedded in an embedding medium, for example paraffin. Each histological section is applied onto a specimen slide, provided a histological section is qualified as usable. The remaining histological sections are usually disposed of as sectioning waste. The specimen slides, with the histological sections applied thereonto, are usually subjected to a further treatment, the histological sections being stained using staining methods and ultimately observed with a microscope.

Section strips usually occur during the sectioning operation; these are formed because a histological section, directly after it is produced, is positioned on the blade holder. When a further histological section is produced, it is in that context likewise moved onto the blade holder, with the result that the previously produced histological section is moved by the further histological section away from the blade of the microtome. Because the further histological section and the previously produced histological section are in contact with one another at their respective edge regions, the thin histological sections adhere to one another and thus form a section strip. This operation is repeated analogously as further histological sections are produced, so that a section strip having multiple histological sections can be formed. Before a suitable histological section can be transferred onto a specimen slide, the section strip must be split up. Assuming that the suitable histological section is the last section that was produced, the previously produced histological section, or all the previously produced histological sections of that section strip, must be separated from the suitable histological section in order to isolate the suitable histological section. This is usually carried out manually by the microtome operator, using a forceps or a paintbrush. Individual histological sections can easily be damaged during this separation operation. This working step accordingly requires a great deal of experience and skill on the part of the microtome operator. The apparatus known from the existing art for isolating histological sections from a section strip thus represents a manually actuated paintbrush or forceps.

SUMMARY OF THE INVENTION

The object underlying the present invention is therefore that of describing and refining an apparatus and a method with which the operation of isolating histological sections can be simplified. It would be desirable, in the context of the isolation of histological sections, for a suitable histological section that is to be transferred onto a specimen slide not to be damaged.

The apparatus according to the invention comprises a nozzle device with which a histological section positioned on the blade holder can be impinged upon by an air stream, the direction and the strength or intensity of the air stream being adjusted in such a way that a previously produced histological section of the section strip, which section is connected to the histological section positioned on the blade holder, is separable therefrom and removable from the blade holder.

In accordance with the present invention, therefore, a nozzle device is provided on the blade holder of the microtome, or the nozzle device acts onto or at the blade holder of the microtome. With the nozzle device, a histological section positioned on the blade holder of the microtome is impinged upon by an air stream, or an air stream is moved past the histological section positioned on the blade holder of the microtome. A previously produced histological section of the section strip can thereby automatically be separated from a histological section produced subsequently thereto, and from the most recently produced histological section. The histological section of the section strip after which separation ultimately occurs depends on the adjustment of the nozzle device. The direction and intensity of the air stream are to be adjusted suitably for this purpose. The nozzle device is preferably adjusted in such a way that only the most recently generated histological section remains behind on the blade holder of the microtome, and the previously created histological section(s) are separated from the most recently produced histological section. Applications in which a separation occurs only after two or more most recently produced histological sections are, however, also conceivable.

The direction and, in particular, the intensity of the air stream can depend on several parameters. As the thickness of the histological sections increases, for example, the intensity of the air stream may need to be set correspondingly higher than is the case with thinner histological sections, so that the desired separation effect can be achieved. In addition, the nature or properties of the embedding medium and/or of the tissue sample can have an influence on the intensity and direction of the air stream. The size of the cross-sectional area of the histological sections can also have an influence on the direction of the air stream, and in particular on the location on the blade holder at which the air stream principally acts. When the histological sections have a larger cross-sectional area, the effective spacing from the microtome blade that is relevant for the air stream may need to be made larger than is the case for histological sections with smaller cross-sectional areas. Further possible parameters that can influence the intensity and direction of the air stream are, for example, the surface finish of the blade holder, the ambient temperature, and/or the atmospheric humidity of the environment. On the one hand, therefore, means can be provided with which the intensity and/or direction of the air stream are modifiable. These means could be adjusted manually by the operator, for example as a function of the desired result, in the context of the sectioning operation. Alternatively or additionally, these means could be adjusted automatically; this requires the provision of corresponding sensors (e.g. to determine the section thickness adjustment of the microtome, the temperature, or the atmospheric humidity) that transfer the respectively ascertained values to a control device that is to be provided. Additionally or alternatively, a camera could be provided with which the histological section(s) that has/have been produced is/are imaged and examined, with the aid of digital image processing, with regard to suitability for further processing. Isolation of the histological sections can thus be automated. The control device controls or regulates the direction and/or intensity of the air stream of the nozzle device as a function of the ascertained values or the acquired images of the histological sections.

In an embodiment, the air stream is blown with the nozzle device to the blade holder. For this, a corresponding air delivery hose can be provided with which the positive pressure generated by a fan is directed to the histological section positioned on the blade holder. Also provided is a removal device with which separated histological sections are removable. The removal device could likewise be embodied in the form on air hose or a tubular component with which air and the sectioning waste are removed from the blade holder.

In a preferred embodiment, the air stream is sucked away from the blade holder with the nozzle device. The air stream is accordingly generated by the fact that negative pressure is generated with a fan or a suitable component, if applicable via a tube, with the result that ambient air is aspirated in the region of the histological section positioned on the blade holder.

The nozzle device could comprise a suction conduit that at least partly surrounds the region at which a histological section produced with the blade is positioned on the blade holder. The suction conduit could, in particular, surround or be arranged directly adjacent to the region where a histological section is positioned immediately after the sectioning operation. The suction conduit can thus constitute the inlet region of the nozzle device, at which region ambient air is aspirated if the nozzle device aspirates the air stream.

According to a very particularly preferred embodiment, the suction conduit comprises a constricted region that is at a predefinable distance from the blade. The predefinable distance could correspond substantially to the diameter or to a longitudinal side of a histological section. The constricted region is preferably embodied to be constricted in a direction perpendicular to the surface of a histological section. As a result of the constricted region on the suction conduit, and a reduced flow cross section associated therewith, the air there exhibits a higher flow velocity than, for example, in a region before it. An elevated air pressure therefore exists in this region, which pressure promotes and/or effects detachment of the corresponding histological section that is located in that region.

Very particularly preferably, the suction conduit is configured in such a way that the location of the constricted region is variably adjustable. This is preferably accomplished in such a way that the shape and/or the geometry of the suction conduit in the inlet region is not, or not substantially, modified. This could be achieved, for example, by way of a deformable wall of the suction conduit that, with suitable means, predefinably modifies the distance from the oppositely located wall of the suction conduit. Alternatively, a curved wall of the suction conduit could be arranged movably relative to the other walls of the suction conduit along a direction, so that the inwardly curved region of the movably arranged wall can be brought respectively to a different position. The constricted region of the suction conduit is then located at that respective position.

The suction conduit could be configured in such a way that it comprises a suction axis. The suction axis of the suction conduit proceeds substantially as an extension of the delivery direction of a histological section, or of the section strip, on the blade holder. What can be achieved thereby is, for example, that the particular histological section most recently produced remains positioned on the blade holder because of the air flow and/or is in fact impinged upon by a slight pressure in the direction of the blade holder.

The suction conduit could remove the histological sections, separated by the air stream, substantially downward. A corresponding shape or layout of the suction conduit is a prerequisite for this. Especially in the case of a conventional rotary microtome, the sectioning waste is removed downward into a section collection pan. If a suction conduit is then provided in the front central region, facing toward the microtome operator and downward from the blade holder, the histological sections and/or the sectioning waste can as a result be removed downward, and operation of the microtome is not substantially impaired by the suction conduit.

The histological sections separated by the air stream are preferably conveyable with the suction conduit to a filter device. The histological sections and/or sectioning waste conveyed to the filter device can in this fashion be disposed of properly together with the filter, especially since the tissue samples contained in the histological sections may be contaminated, and thus give rise to a health risk for an operator of the microtome.

According to a very particularly preferred embodiment, the nozzle device is embodied and arranged in such a way that air is aspirated in the sectioning region in order to prevent the histological section from rolling up or creasing, and/or to position the histological section on the blade holder. This can be achieved, for example, by the fact that the nozzle device and/or the suction conduit is or are shaped and positioned in such a way that for a predefinable intensity of the air stream, a histological section, in particular the most recently produced histological section, is pressed against the blade holder and positioned or retained there. High quality for the histological sections produced can thus advantageously be ensured, since they exhibit no creases or similar undesirable artifacts.

For reproducible utilization of the isolation apparatus according to the present invention it is helpful if, upon production of a histological section, a previously produced histological section is moved along the blade holder and in that context taken away from the blade. This is achieved, as a rule, by the fact that the histological section to be produced most recently, as it is produced, moves or shifts the previously produced histological section away from the blade. A section strip is then, as a rule, also formed.

Very particularly preferably, the histological sample or tissue sample is embedded in an embedding medium. A block is thereby formed. The cross section of the block is round and, in particular, of circular configuration. In other words the block, in the context of a circular cross section, preferably has a cylindrical or a truncated conical shape. The cross section or shape of a histological section from such a block is accordingly round or circular. When such histological sections form a section strip, because of the round or circular cross sections they are therefore connected to one another only at connecting points that extend over a smaller region (ideally, for example, only at one contact point) than is the case for histological sections of rectangular cross section (in which the connecting point of two histological sections extends over an entire adjacent side surface). A section strip made up of histological sections having a round or circular cross section can therefore be split up more easily. A comparatively smaller air stream from the nozzle device can accordingly be sufficient to split up a section strip in a desired fashion.

The positive or negative pressure of the air stream could be generated with a blower, a fan, a compressor, or a pump; the blower, fan, compressor, or pump could be arranged on the microtome or in its immediate vicinity. The air stream can preferably be generated in variably adjustable fashion with the respective device for generating the positive or negative pressure.

The isolated histological section could be conveyed manually for further processing. This could be accomplished, for example, by the fact that the microtome operator picks up the isolated (most recently produced) histological section with the aid of a forceps and transfers it into a water bath, in order then to apply the histological section onto a specimen slide. Direct manual application of the histological section onto a specimen slide could also be accomplished if the histological section on the blade holder is not creased or corrugated. According to a very particularly preferred embodiment, however, a histological section is applied onto a specimen slide with an application apparatus as provided in one of Claims 1 to 19 of DE 10 2007 047 797.1. The entire disclosure of DE 10 2007 047 797.1 is thus incorporated hereinto, and reference is made thereto. With this application apparatus, a histological section positioned on the blade holder—in particular the isolated, mostly recently produced histological section—is applied directly onto a specimen slide. The application apparatus comprises a positioning device with which the specimen slide is transferable from an initial position into an application position. With the specimen slide in the application position, the histological section positioned on the blade holder can be brought at least partly into contact with the surface of the specimen slide. The histological section can thereby be applied onto the specimen slide. This can be accomplished in automated fashion, or by manual actuation by the microtome operator. The specimen slide or application apparatus, and/or the positioning device, can be provided on or integrated onto the nozzle device. In particular, the specimen slide could be part of the wall of the nozzle device or of the suction conduit that, in its initial position, seals the nozzle device externally. Because a specimen slide is, as a rule, made of glass and is thus transparent, the histological section or sections can be viewed by the microtome operator through the nozzle device or the specimen slide.

The air stream is preferably shut off or reduced when the histological section positioned on the blade holder is to be applied onto a specimen slide or is intended for further processing. This action can ensure that the sensitive operation of applying the histological section onto a specimen slide, or taking the histological section off the blade holder, is not disrupted or impaired. Shutoff or reduction of the air stream is preferably accomplished on the basis of an operator input and/or in automated fashion.

As already indicated, the application apparatus is preferably integrated onto the nozzle device and/or onto the apparatus. This may be necessary or advisable for sealing of the nozzle device, and/or result in a compact design. In comparable fashion, the nozzle device, at least part of the apparatus, and/or at least a subregion of the suction conduit could be installed on the blade holder or integrated thereonto.

According to a preferred embodiment, the nozzle device and/or the suction conduit is/are arranged in stationary fashion relative to the blade holder. It is thereby possible to ensure that, in particular, the direction of the air stream can impinge upon a histological section in reproducible fashion and/or that the direction of the air stream cannot be manipulated, or can be manipulated only within certain limits, by an operator. This action, as well, can make possible a compact design.

The invention includes also a microtome. In accordance therewith, the microtome serves for the production of histological sections. The histological sections can be produced in such a way that a histological section that is produced is connected to a previously produced histological section to form a section strip. The microtome is characterized by an isolation apparatus for isolating histological sections. The isolation apparatus comprises a nozzle device, preferably provided on the blade holder of the microtome, with which a histological section positioned on the blade holder can be impinged upon by an air stream. The direction and intensity of the air stream are adjusted in such a way that a previously produced histological section of the section strip, which section is connected to the histological section positioned on the blade holder, is separable therefrom and removable from the blade holder. The microtome could be embodied in the form of a rotary microtome, a sliding microtome, or a rotating disc microtome. The microtome comprises, in particular, an isolation apparatus as described in detail above, so that in order to avoid repetition, reference is made to the foregoing portion of the Specification.

The invention includes also a method serving to isolate histological sections produced with a microtome. The histological sections are produced in such a way that a histological section that is produced is connected to a previously produced histological section to form a section strip. The method according to the present invention is characterized in that with a nozzle device (preferably provided on the blade holder of the microtome and/or acting on the blade holder) of an isolation apparatus, a histological section positioned on the blade holder is impinged upon by an air stream. The direction and intensity of the air stream are adjusted in such a way that a previously produced histological section of the section strip, which section is connected to the histological section positioned on the blade holder, is separated therefrom and removed from the blade holder.

The method according to the present invention serves in particular for operating an apparatus as describe in detail above. Alternatively or additionally, the method according to the present invention serves for operating a microtome. In order to avoid repetition, reference is therefore made to the foregoing portion of the Specification regarding the apparatus features relevant thereto. The method steps necessary for operating the apparatus are apparent in this context to a skilled artisan active in the present sector having a knowledge of the disclosure of the foregoing portion of the Specification.

There are various ways of advantageously embodying and refining the teaching of the present invention. Below preferred exemplifying embodiments of the invention are explained in more detail with reference to the drawings. In conjunction with the explanation of the preferred exemplifying embodiments of the invention with reference to the drawings, an explanation is also given of generally preferred embodiments and refinements of the teaching.

DETAILED DESCRIPTION OF THE DRAWINGS

Figure 1:
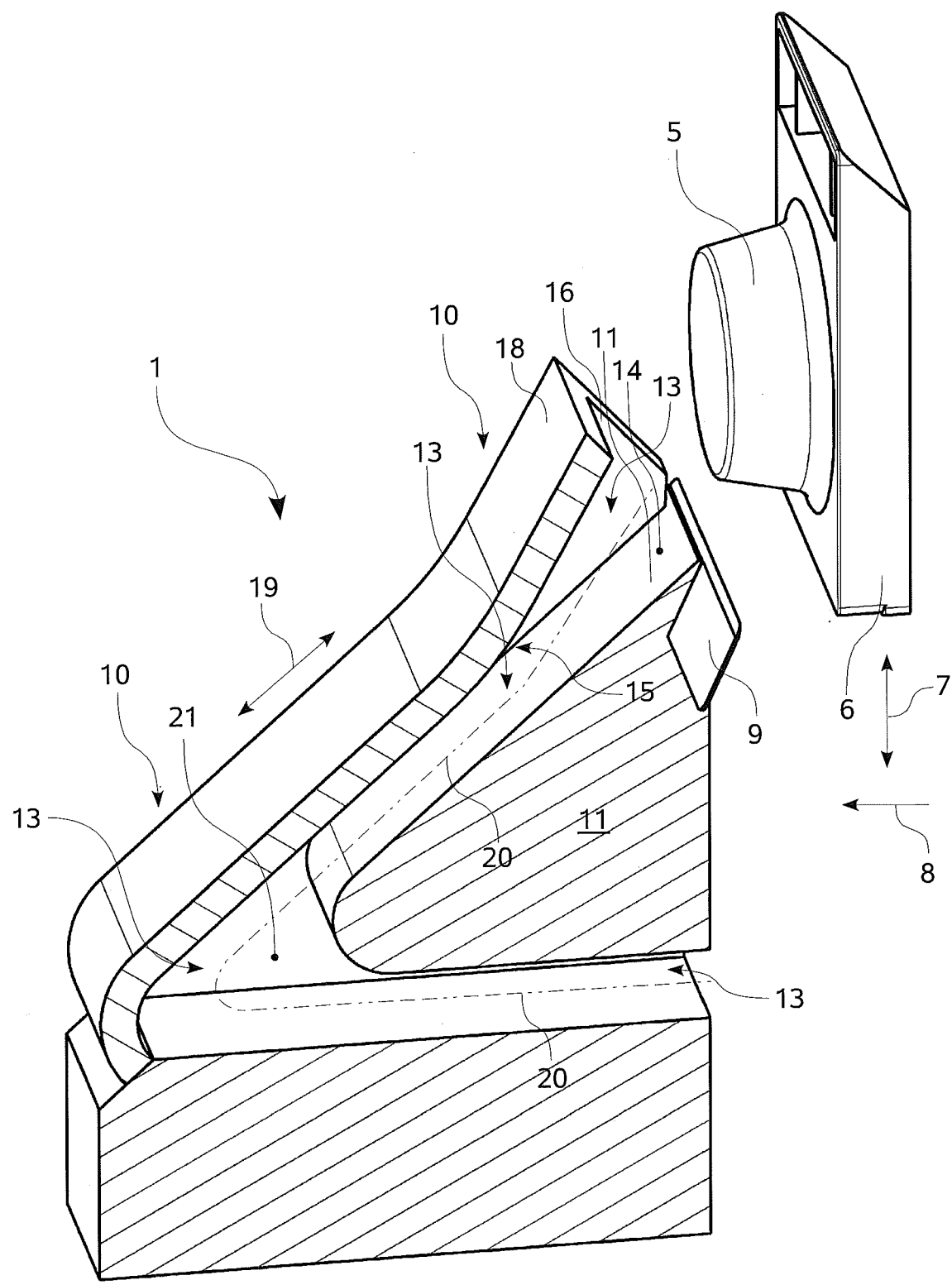
FIG. 1 is a perspective view of an exemplifying embodiment of an apparatus according to the present invention for isolating histological sections.
Figure 2:
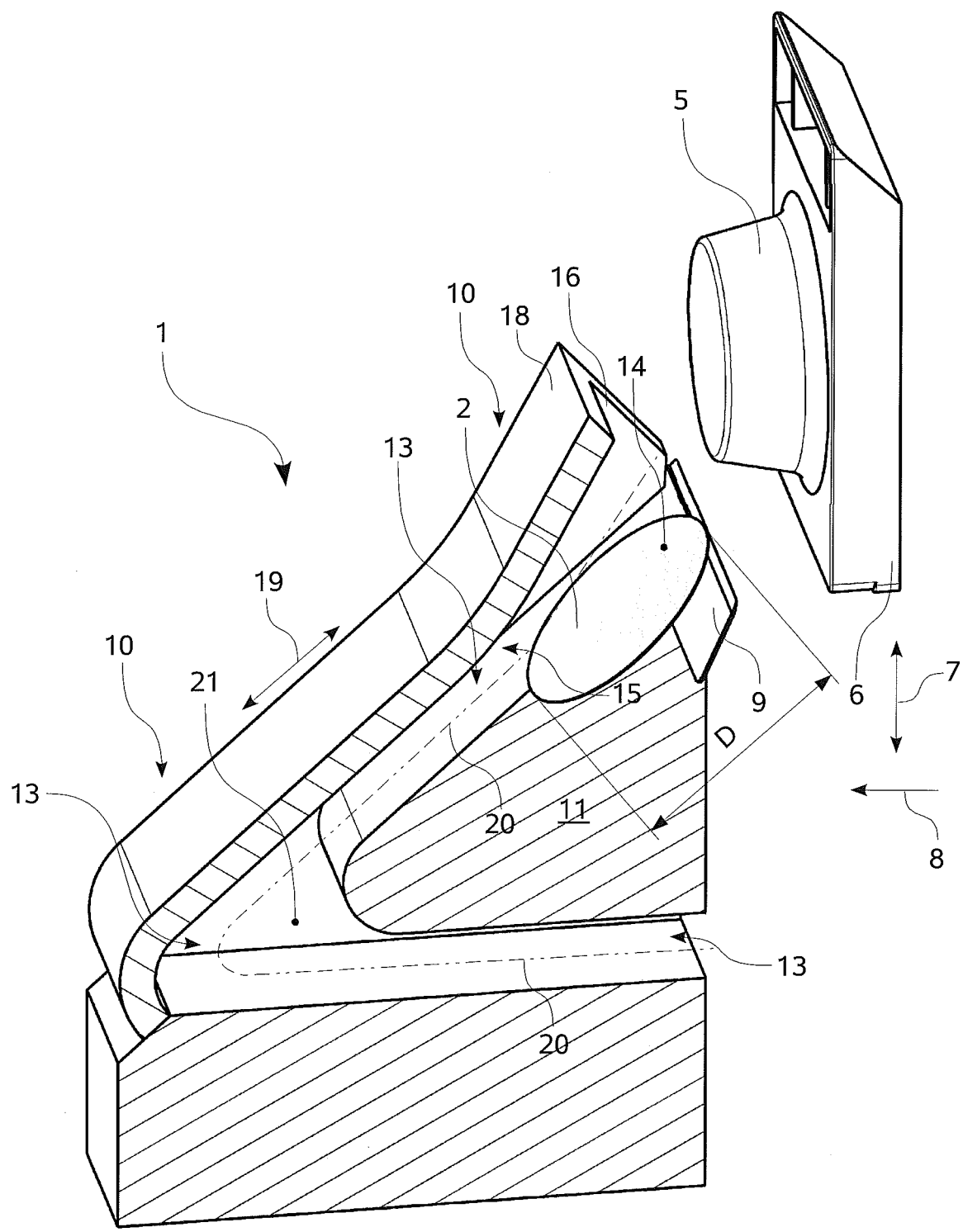
FIG. 2 shows the exemplifying embodiment of FIG. 1, a histological section having been produced and being positioned on the blade holder.
Figure 3:
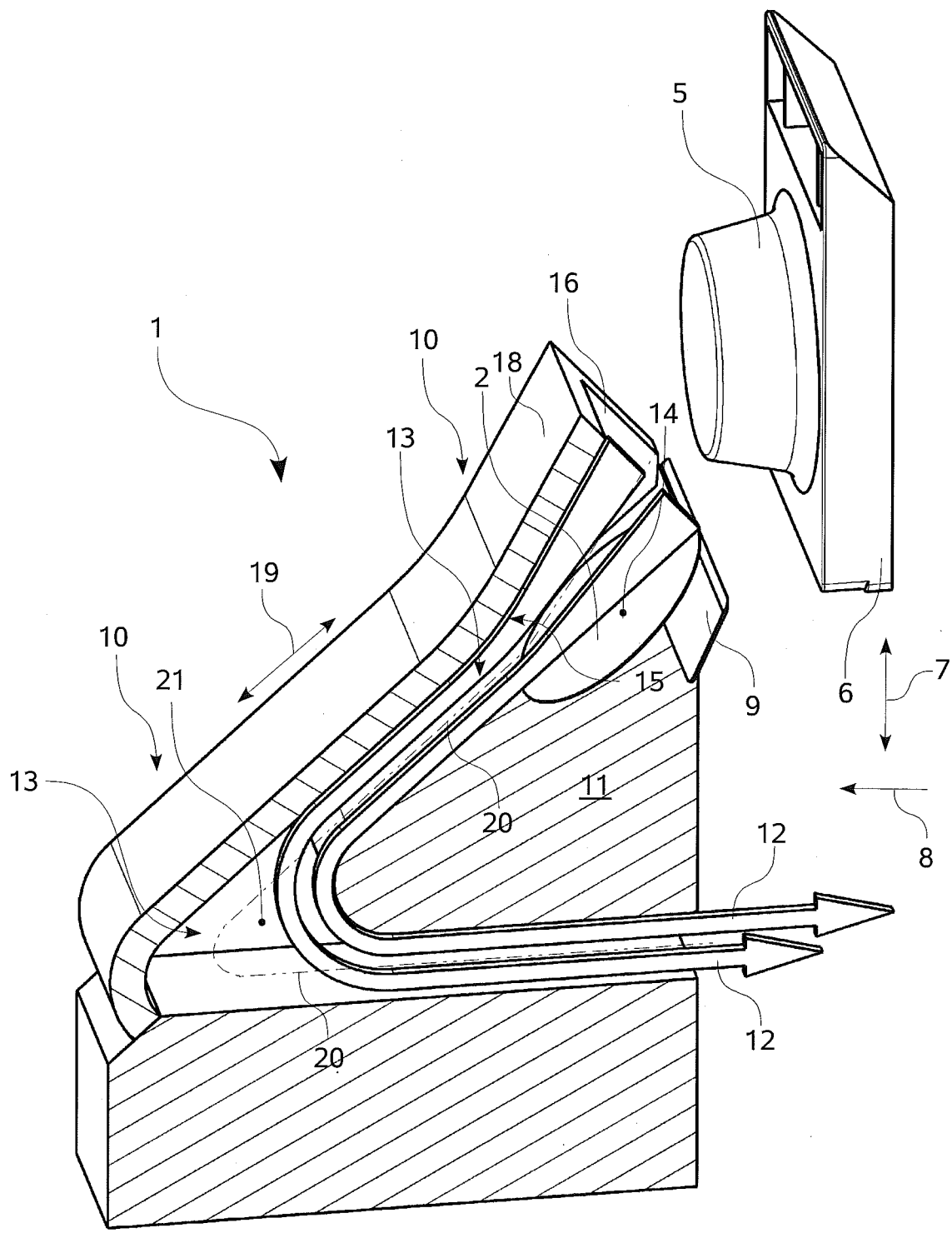
FIG. 3 shows the exemplifying embodiment of FIG. 1, the air stream being indicated schematically with arrows.
Figure 4:
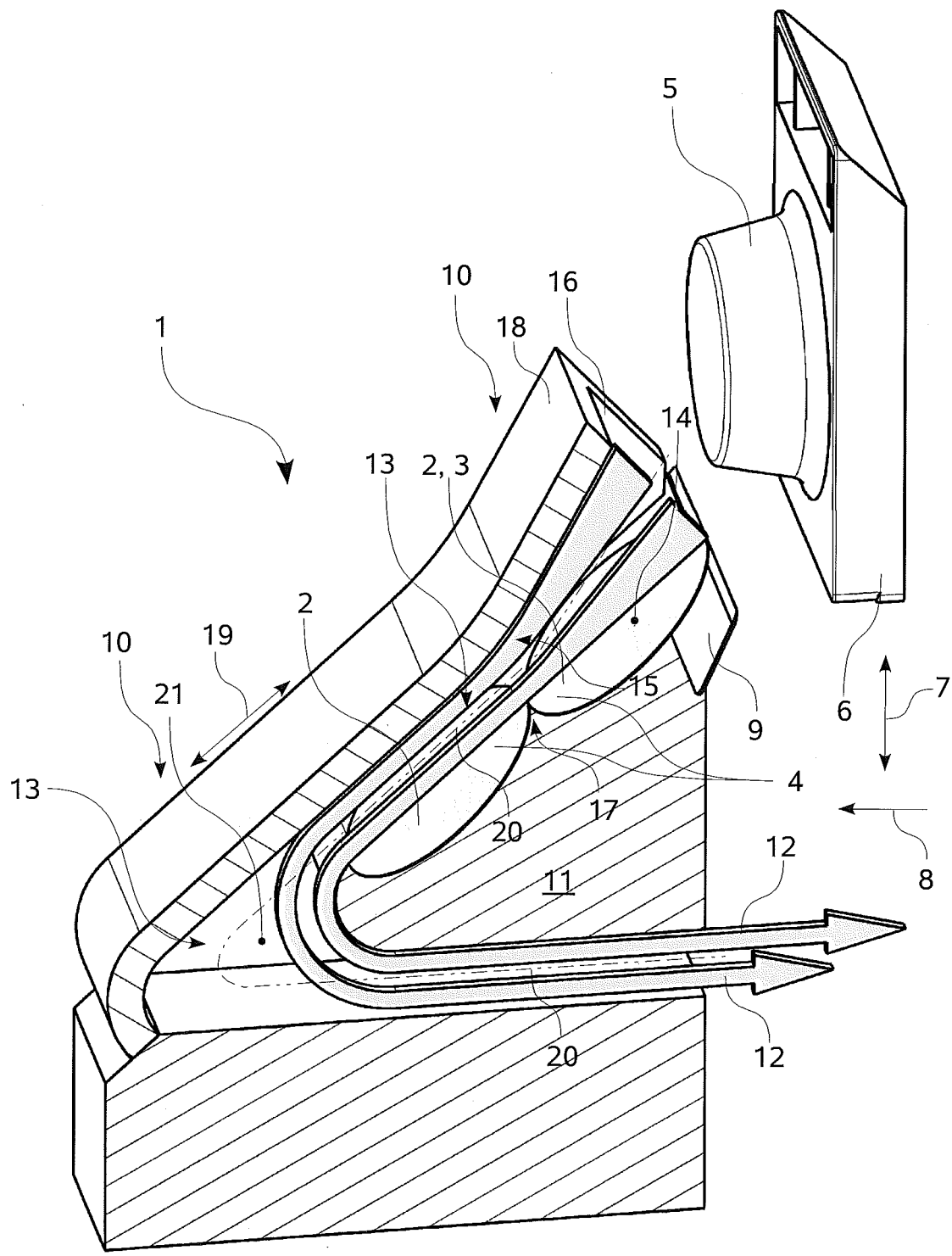
FIG. 4 shows the exemplifying embodiment of FIG. 1, two histological sections having been produced and forming a section strip.

In the Figures, identical or similar components are labeled with the same reference characters. FIGS. 1 to 5 each show an apparatus 1 for isolating histological sections 2. Apparatus 1 for isolating histological sections 2 is, in these exemplifying embodiments, a constituent of a microtome (not shown in the Figures). Histological sections 2, 3 are produced in such a way that a most recently produced histological section 3 is connected to a previously produced histological section 2 to form a section strip 4 (see FIG. 4). A section strip 4 can usually comprise several histological sections 2, 3. FIG. 4 shows only two histological sections 2, 3 connected to form a section strip 4. Upon production of a histological section 3, a previously produced histological section 2 is moved or shifted along on blade holder 11 by the most recently produced histological section 3. The previously produced histological section 2 is thereby moved away from blade 9.

Histological sections 2, 3 were produced from block 5, block 5 containing a histological sample (not shown in the Figures) that is embedded in an embedding medium. It may be inferred from the perspective depictions in FIGS. 1 to 4 that block 5 has a substantially circular cross section and has the shape of a truncated cone. Histological sections 2, 3 thus likewise each have a circular cross section. Block 5 is mounted on a cassette 6. Cassette 6 in turn is clamped in a specimen holder (not shown in the Figures) of a microtome. The specimen holder, together with cassette 6 and block 5, is moved upward and downward in a vertical direction (arrow 7) so that—assuming appropriate specimen advance by a predefinable amount in direction 8 in each case—a histological section 2, 3 is produced as block 5 passes by blade 9 of the microtome. The microtome is accordingly configured in the form of a rotary microtome. The basic manner of operation of a rotary microtome is described, for example, in DE 103 52 578 B3.

In accordance with the present invention, an apparatus 1 is provided that encompasses a nozzle device 10. With nozzle device 10, a histological section 2 positioned on blade holder 11 can be impinged upon by an air stream 12 (see e.g. FIG. 3). The direction and intensity of air stream 12 are adjusted in such a way that a previously produced histological section 2 of section strip 4 (see FIG. 4), which section is connected to histological section 3 positioned on blade holder 11, is separable from that section and removable from blade holder 11 with the aid of nozzle device 10. This separated state of histological sections 2, 3 is shown, for example, in FIGS. 2 and 3, where only the most recently produced histological section is positioned on blade holder 11. The two histological sections 2, 3 are connected at connecting point 17 to form section strip 4. For illustrative reasons, both histological sections 2, 4 of section strip 4 are shown, without isolation, in FIG. 4.

Air stream 12 is aspirated away from blade holder 11 with nozzle device 10. Nozzle device 10 comprises a suction conduit 13 that at least partly surrounds region 14 at which a histological section 2, 3 produced with blade 9 is positioned on blade holder 11.

Suction conduit 13 comprises a constricted region 15, suction conduit 13 being embodied with a constriction substantially in a direction perpendicular to the surface of blade holder 11 and of histological section 2. Concretely, suction conduit 13 or nozzle device 10 exhibits a rectangular cross section at intake part 16. Wall 18 of suction conduit 13 arranged opposite blade holder 11 is arranged with its inner surface at an angle to the surface of blade holder 11. The cross section of suction conduit 13 thus decreases from intake part 16 to constricted region 15. Constricted region 15 is at a predefinable distance from blade 9, which distance corresponds substantially to diameter D of a histological section 2, 3.

Although this is not explicitly shown in the Figures, suction conduit 13 could be embodied in such a way that the location of constricted region 15 is variably adjustable. This could be implemented, for example, with the aid of vane elements instead of wall 18, or by the provision, instead of wall 18, of a wall element displaceable in direction 19. A separation of the section strip only after two, three, or more histological sections can thereby be achieved, for example, if this should be necessary for application-specific reasons.

Suction conduit 13 has a suction axis 20 that, at least in constricted region 15, proceeds substantially as an extension of the delivery direction of a histological section 2, 3 on the blade holder. Suction conduit 13 removes the further histological sections 2 firstly downward and in direction 8. After curved region 21 of suction conduit 13, histological sections 2 are removed substantially in a horizontal direction, opposite to direction 8, away from the operator of the microtome and below blade holder 11, and to the rear through the microtome. The further histological sections 2 and 3 are thus deliverable with suction conduit 13 to a filter device 22 (shown only schematically in FIG. 5). The negative pressure for generating air flow 12 is generated with a fan 23 (indicated merely schematically in FIG. 5). An operator operates the microtome from the left side of apparatus 1 shown in FIG. 1.

Nozzle device 10, and in particular suction conduit 13, are embodied and arranged in such a way that air is aspirated in the sectioning region in the immediate vicinity of blade 9, in order to prevent rolling or creasing of histological section 2 or 3 (which is arranged adjacent to blade 9) and to position histological section 2 or 3 on blade holder 11.

Figure 5:
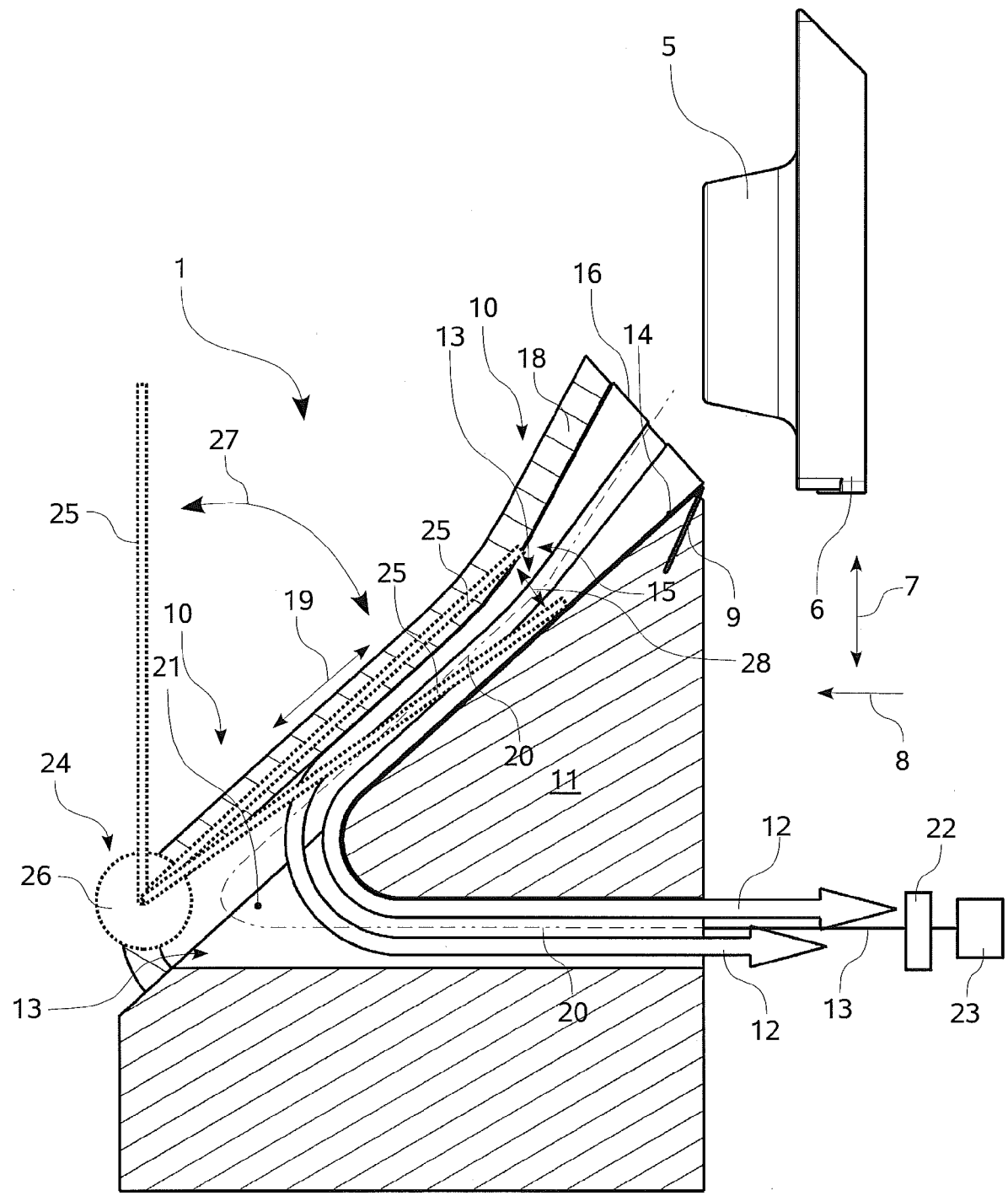
FIG. 5 is a cross-sectional view showing the exemplifying embodiment of FIG. 1 additionally with an application apparatus.

An application apparatus 24 described in DE 10 2007 047 797.1, with which histological section 2 or 3 positioned on blade holder 11 is transferable onto a specimen slide 25, is indicated merely schematically and with dashed lines in FIG. 5. Specimen slide 25 is arranged pivotably (in arrow directions 27 and 28) in this context, and in one position can be flush with wall 18. This is the initial position of specimen slide 25. For the application of histological section 2 onto specimen slide 25, specimen slide 25 is pivoted, with rotatably mounted component 26 of application apparatus 24, toward blade holder 11 along arrow 28, in which context histological section 2 comes into contact with the surface of specimen slide 25. In this exemplifying embodiment, only one histological section 2 according to FIG. 4 can be applied onto specimen slide 25, since specimen slide 25 in its application position is spaced too far away from blade 9. As soon as histological section 2 adheres, by adhesive force, onto specimen slide 25, specimen slide 25 can be pivoted with the aid of the rotatably mounted component 26 into a position (shown as vertical in FIG. 5) in which the operator can remove specimen slide 25 along with a histological section 2 applied thereonto. Because specimen slide 25 is made of glass, suction conduit 13 and blade holder 11, and histological sections 2 or 3 positioned thereon, can be viewed by an operator through wall 18 or through specimen slide 25. When a histological section 2 is to be applied onto a specimen slide 25, air stream 12 is shut off on the basis of an operator input.

Application apparatus 24 indicated in FIG. 5 is integrated onto nozzle device 10 or onto apparatus 1. Nozzle device 10 and a subregion of suction conduit 13 are integrated onto blade holder 11. Nozzle device 10 and suction conduit 13 are arranged in stationary fashion relative to blade holder 11.

In conclusion, be it noted very particularly that the exemplifying embodiments discussed above serve merely to describe the teaching claimed, but do not limit it to the exemplifying embodiments.

LIST OF REFERENCE NUMERALS

1 Isolation apparatus
2 (Previously produced) histological section
3 (Most recently produced) histological section
4 Section strip
5 Block
6 Cassette
7 Vertical direction of movement of the sample
8 Direction of sample advance
9 Blade
10 Nozzle device
11 Blade holder
12 Air stream
13 Suction conduit
14 Region in which a histological section 2, 3 produced with a blade 9 is positioned on the blade holder 11
15 Constricted region of aforementioned region 14
16 Intake part of the suction conduit 13
17 Connecting point between the histological sections 2 and 3
18 Wall of the suction conduit 13, arranged opposite the blade holder 11
19 Displacement direction of wall element
20 Suction axis of the suction conduit 13
21 Curved region of the suction conduit 13
22 Filter device
23 Fan
24 Application apparatus
25 Specimen slide
26 Rotatably mounted component of the application apparatus 24
27 Rotation direction of the specimen slide 25 between its initial and removal position
28 Rotation direction of the specimen slide 25 between its initial position and application position
D Diameter of the histological sections 2 and 3

The invention claimed is:

1. An apparatus for isolating histological sections produced with a microtome, said microtome comprising a blade holder, wherein the histological sections are producible so that a currently produced histological section is directly connected to a previously produced histological section at a connecting point between the currently produced histological section and the previously produced histological section to form a section strip where the currently produced histological section and the previously produced histological section are in direct contact with each other, said apparatus comprising:

a nozzle device comprising a suction conduit that at least partly surrounds the region at which the histological section produced with the blade is positioned on the blade holder for subjecting the histological sections positioned on the blade holder to an air stream and sucking away the air stream from the blade holder; wherein the air stream is adjustable for adjusting at least one of a direction and intensity of the air stream for separating the previously produced histological section from the currently produced histological section and removing it from the blade holder when the currently produced histological section is positioned on that blade holder by at least one of a variably adjustable constricted region of the suction conduit; and one of the group consisting of a blower, a fan, a compressor and a pump variably adjusting the air stream intensity in the suction conduit that is generated by at least one of said group; and the apparatus further comprises:

an application apparatus with a rotatable mounted component adapted to receive a specimen slide and pivot the specimen slide toward the blade holder for applying the histological section onto the specimen slide.

2. The apparatus according to claim 1, wherein the direction of the nozzle device is adjustable so that it blows the air stream to the blade holder; and a removal device for removing the separated histological sections.

3. The apparatus according to claim 1, wherein the suction conduit comprises in a direction substantially perpendicular to the surface of one of the histological sections a constricted region provided at a predefined distance from the blade that is substantially the diameter or the longitudinal side of that histological section.

4. The apparatus according to claim 3, wherein the position of the constricted region of the suction conduit is variably adjustable.

5. The apparatus according to claim 1, wherein the suction conduit comprises a suction axis extending substantially as an extension of a delivery pathway of the histological sections to the blade holder.

6. The apparatus according to claim 1, wherein the suction conduit extends in vertical direction downstream from the blade holder substantially downwards so that the histological sections separated by the air stream are removed in vertical direction substantially downwards.

7. The apparatus according to claim 1, comprising a filter device that is designed to receive the histological sections separated by the air stream and conveyed via the suction conduit to the filter device.

8. The apparatus according to claim 1, wherein the nozzle device is designed and arranged such that air is aspirated in the sectioning region in order to prevent the histological section from rolling up or creasing and to position the histological section on the blade holder.

9. The apparatus according to claim 1, wherein the histological sample is embedded in an embedding medium and a block is thereby formed; and the cross section of the block is round.

10. The apparatus according to claim 1, wherein the air stream can be shut off or reduced when the histological section positioned on the blade holder is to be applied onto a specimen slide or is intended for further processing.

11. The apparatus according to claim 1, wherein the application apparatus is provided as part of the nozzle device.

12. The apparatus according to claim 1, wherein the nozzle device or at least a subregion of the suction conduit is part of the blade holder.

13. The apparatus according to claim 1, wherein the nozzle device or the suction conduit is arranged in stationary fashion relative to the blade holder.

14. A method performed by the apparatus as claimed in claim 1 for isolating histological sections produced with a microtome, said method comprising: cutting the previously produced histological section; cutting the currently produced histological section connected to the previously produced histological section; adjusting at least one of the direction and intensity of the air stream and subjecting the section strip to that air stream when placed on the blade holder; separating the previously produced histological section from the currently produced histological section by means of the airstream; removing the previously produced histological section from the blade holder by means of the airstream; receiving a specimen slide in a rotatably mounted component in an application apparatus; and pivoting the specimen slide toward the blade holder for applying the histological section onto the specimen slide.

15. The method according to claim 14, further comprising the method steps of providing and arranging the nozzle device and aspirating air through the nozzle device so that rolling up or creasing of the histological sections is prevented and these are placed on the blade holder.

16. The method according to claim 14, further comprising the method step of applying the histological section positioned on the blade holder onto a specimen slide by means of an application apparatus.

17. The method according to claim 14, further comprising the method step of shutting off or reducing the air stream when the histological section positioned on the blade holder is applied onto a specimen slide.

\* \* \* \* \*

UNITED STATES PATENT AND TRADEMARK OFFICE
CERTIFICATE OF CORRECTION

PATENT NO.      : 8,728,799 B2  
APPLICATION NO. : 12/349321  
DATED           : May 20, 2014  
INVENTOR(S)     : Christoph Schmitt Page 1 of 1

It is certified that error appears in the above-identified patent and that said Letters Patent is hereby corrected as shown below:

In the Claims

Column 10, line 10 reads:

an application apparatus with a rotatable mounted compoand should read:

an application apparatus with a rotatably mounted compo-

Signed and Sealed this  
Twenty-second Day of July, 2014

Michelle K. Lee  
*Deputy Director of the United States Patent and Trademark Office*